(12) United States Patent
Gebauer

(10) Patent No.: US 10,449,350 B2
(45) Date of Patent: Oct. 22, 2019

(54) CONNECTOR FOR ASEPTIC CONNECTION

(71) Applicant: GE Healthcare Bio-Sciences AB, Uppsala (SE)

(72) Inventor: Klaus Gebauer, Uppsala (SE)

(73) Assignee: GE HEALTHCARE BIO-SCIENCES AB, Uppsala (SE)

(*) Notice: Subject to any disclaimer, the term of this patent is extended or adjusted under 35 U.S.C. 154(b) by 301 days.

(21) Appl. No.: 15/032,249

(22) PCT Filed: Nov. 5, 2014

(86) PCT No.: PCT/SE2014/051307
§ 371 (c)(1),
(2) Date: Apr. 26, 2016

(87) PCT Pub. No.: WO2015/069176
PCT Pub. Date: May 14, 2015

(65) Prior Publication Data
US 2016/0235962 A1    Aug. 18, 2016

(30) Foreign Application Priority Data

Nov. 7, 2013    (SE) ..................... 1351314

(51) Int. Cl.
*F16L 55/24*    (2006.01)
*A61M 39/10*    (2006.01)
(Continued)

(52) U.S. Cl.
CPC ........ *A61M 39/1055* (2013.01); *A61M 39/10* (2013.01); *A61M 39/16* (2013.01);
(Continued)

(58) Field of Classification Search
CPC ... F16L 55/24; F16L 2201/40; F16L 2201/44; F16L 2201/80
(Continued)

(56) References Cited

U.S. PATENT DOCUMENTS 3,142,499 A * 7/1964 Lang ..................... F16L 58/184
277/614
3,865,411 A   2/1975 Rowe et al.
(Continued)

FOREIGN PATENT DOCUMENTS

CN    101400401 A    4/2009
CN    102401206 A    4/2012
(Continued)

OTHER PUBLICATIONS

International Preliminary Report on Patentability received for PCT Patent Application No. PCT/SE2014/051307, dated May 10, 2016, 6 pages.
(Continued)

*Primary Examiner* — Aaron M Dunwoody
(74) *Attorney, Agent, or Firm* — Wood IP LLC

(57) ABSTRACT

Provided is a connector for substantially aseptic connection of tubing, that includes a central tubular stem member with a line connection end and a coupling end having an annular gasket arranged to engage a similar annular gasket on a similar second connector in sealing abutment and a tubular socket member, concentrically arranged outside the stem member, having a flange concentrically arranged outside the coupling end and a cover film releasably bonded to the flange and covering the coupling end of the stem member, the annular gasket and at least a portion of the flange. The socket member is rotatable around the stem member and the connector also has an annular seal member in sealing abutment between an inside of the socket member and an outside of the stem member.

10 Claims, 3 Drawing Sheets

(51) Int. Cl.
*A61M 39/18* (2006.01)
*A61M 39/16* (2006.01)
*C12M 1/12* (2006.01)

(52) U.S. Cl.
CPC .......... *A61M 39/165* (2013.01); *A61M 39/18* (2013.01); *A61M 2039/1027* (2013.01); *C12M 37/04* (2013.01); *F16L 2201/44* (2013.01)

(58) Field of Classification Search
USPC ..................................................... 285/3, 336
See application file for complete search history.

(56) References Cited

U.S. PATENT DOCUMENTS

| | | | |
|---|---|---|---|
| 4,019,512 A | 4/1977 | Tenczar | |
| 4,187,846 A * | 2/1980 | Lolachi | A61M 39/14 |
| | | | 285/3 |
| 5,287,730 A * | 2/1994 | Condon | G01M 3/022 |
| | | | 138/94.3 |
| 5,492,147 A | 2/1996 | Challender et al. | |
| 6,655,655 B1 * | 12/2003 | Matkovich | A61M 39/1011 |
| | | | 251/149.1 |
| 7,918,243 B2 | 4/2011 | Diodati et al. | |
| 9,851,037 B2 * | 12/2017 | Whitaker | F16L 29/007 |
| 2003/0030272 A1 * | 2/2003 | Johnson | A61M 39/18 |
| | | | 285/3 |
| 2005/0150546 A1 | 7/2005 | Liepold et al. | |
| 2006/0252298 A1 * | 11/2006 | Biddel | A61M 39/16 |
| | | | 439/405 |
| 2008/0048436 A1 | 2/2008 | Matkovich et al. | |
| 2010/0230950 A1 | 9/2010 | Williams et al. | |
| 2012/0061954 A1 * | 3/2012 | Stell | A61M 39/1011 |
| | | | 285/330 |
| 2013/0289517 A1 * | 10/2013 | Williams | F16L 37/098 |
| | | | 604/500 |
| 2015/0061282 A1 * | 3/2015 | Faldt | A61M 39/18 |
| | | | 285/124.5 |
| 2016/0186906 A1 * | 6/2016 | Blake | A61M 39/1011 |
| | | | 285/319 |

FOREIGN PATENT DOCUMENTS

| | | |
|---|---|---|
| EP | 3065814 A1 | 9/2016 |
| JP | 2011515197 A | 5/2011 |
| JP | 2012013151 A | 1/2012 |
| WO | 2008094707 A1 | 8/2008 |
| WO | 2009/002468 A1 | 12/2008 |
| WO | 2013/147688 A1 | 10/2013 |
| WO | 2015/069176 A1 | 5/2015 |

OTHER PUBLICATIONS

Extended European Search Report received for European Patent Application No. 14859742.0, dated Apr. 3, 2017, 6 pages.
International Search Report and Written Opinion regarding International Application No. PCT/SE2014/051307, dated Feb. 27, 2015, 9 pages.
Japan Notice of Preliminary Rejection for Japanese Patent Application No. 2016-526867, dated Oct. 9, 2018, 5 pages.
Chinese Office Action and Search Report Received for Chinese Patent Application 201480061121.5 dated Sep. 29, 2018, 13 Pages (7 pages Official Copy + 6 Pages English Translation).

* cited by examiner

CONNECTOR FOR ASEPTIC CONNECTION

TECHNICAL FIELD OF THE INVENTION

The present invention relates to connectors, and more particularly to aseptic connectors for use e.g. bioprocessing. The invention also relates to systems connected with aseptic connectors.

BACKGROUND OF THE INVENTION

The biotechnology industry uses different manufacturing systems for creating aseptic and sterile connections between process containers and equipment, such as plastic bags and pumps. A known manufacturing system uses controlled environments such as clean rooms or cabinets to ensure aseptic connections during manufacture. When necessary connections are made in such a controlled environment that breaches sterile tubing and piping, the environment does not contaminate the fluid flow passage. However, maintaining a clean room is time consuming, difficult and costly to validate.

Another known manufacturing system uses disposable plastic bags connected to flexible thermoplastic tubing, which requires special connections to assure that the bags and tubes remain clean and sterile. A sterile tube welding machine can be used to weld the thermoplastic tubing in a sterile manner without the need for a clean room, a laminar flow cabinet or similar environmental control device. After the thermoplastic tubes cool, a sterile weld is formed. A tube welding machine is however also usually limited in applicability to specific tube size and materials, such as thermoplastic tubing. Furthermore, tube welding machines are typically large, heavy, lack versatility, and expensive. Known are also pre-sterile bags and tube sets which can be supplied with the appropriate disposable aseptic connection system fittings already in place. These, connections are simple, repeatable and validatable. Single use systems, also called disposable systems, are more and more used in the bioprocess industry. For example separation or reaction systems such as chromatography systems, filter systems or bioreactor systems have today at least partly been provided as disposable systems. This eliminates the need for cleaning and cleaning validation before processing, in between processes and cycles or after processing before re-use as required for conventional re-usable equipment. With disposable systems cross-contamination is avoided.

Bioburden control of single-use equipment during manufacturing of the equipment itself is required to eliminate cleaning needs before bringing single-use equipment into product contact. This is usually achieved by manufacturing of single-use equipment in controlled environment (clean room), often followed by sterilization processes (gamma irradiation). The demands of the level of bioburden control can differ for different applications. However, bioburden control to a certain degree of the equipment is not only required for some applications, but also considered as the preferable for most of the applications using disposable equipment. The production of this equipment in controlled environments is required to guarantee a low initial level of contaminants prior to the bioburden control procedure. Sterility and asepsis are terms used to define the state of a system, a piece of equipment or a fluid conduit as being in control of bioburden levels to different degrees.

Prior art describes varying apparatus for accomplishing sterile connections using disposable aseptic connectors. Typically the sterility of the connector before establishment of connection is ensured by a releasably bonded cover film which can be removed together with the cover film of a mating connector when they are connected or at a close distance to each other. Such connectors have been described in e.g. U.S. Pat. No. 6,679,529, WO 2009/002468 and WO 2013/147688, which are hereby incorporated by reference in their entireties. They are also commercially available from GE Healthcare under the name of ReadyMate™.

The connectors described above have to be facing each other in particular directions to allow connection, in that the cover films of both connectors have to be pulled out together in the same direction. As the connectors are also fixed at one end to the tubing, it is an issue that the tubing with the connectors may have to be twisted to allow connection. This is undesirable, particularly when complex bioprocessing equipment is to be connected with large diameter tubing.

Accordingly there is a need for connectors that do not require twisting of the tubing.

SUMMARY OF THE INVENTION

One aspect of the invention is to provide an aseptic connector which allows easy rotation around its longitudinal axis. This is achieved with a connector for substantially aseptic connection of tubing, that includes a) a central tubular stem member having a line connection end and a coupling end with an annular gasket arranged to engage a similar annular gasket on a similar second connector in sealing abutment and b) a tubular socket member, concentrically arranged outside said stem member, having a flange concentrically arranged outside said coupling end and comprising a cover film releasably bonded to said flange and covering said coupling end of said stem member, said annular gasket and at least a portion of said flange. The socket member is rotatable around said stem member and said connector further includes an annular seal member in sealing abutment between an inside of said socket member and an outside of said stem member.

One advantage is that the connector is easy to use also with large diameter tubing and in complex bioprocessing settings. A further advantage is that aseptic conditions are well maintained without cleanrooms or sterile cabinets.

Another aspect of the invention is to provide an aseptic system connected with a pair of connectors. This is achieved with a connection as defined in the claims.

Further suitable embodiments of the invention are described in the dependent claims.

Definitions

The terms aseptic and sterile are herein used interchangeably and mean that the concentration of viable microorganisms is reduced compared to ambient conditions. The concentration can e.g. be less than 10%, less than 1% or less than 0.1% of the ambient concentration.

DRAWINGS

DETAILED DESCRIPTION OF EMBODIMENTS

Figure 1:
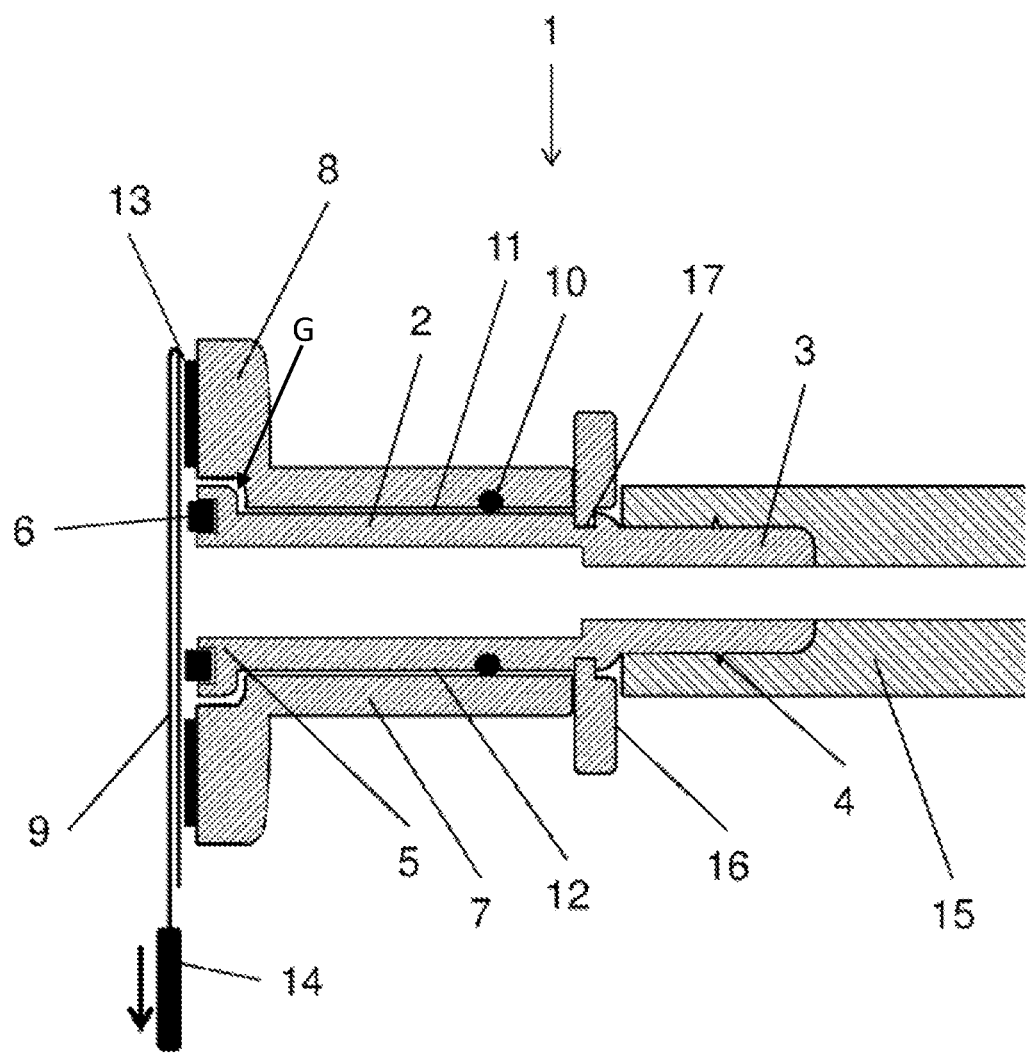
FIG. 1 shows a connector of the invention.

As shown in FIG. 1, in one aspect the present invention discloses a connector 1 for substantially aseptic or for aseptic connection of tubing.

Figure 2:
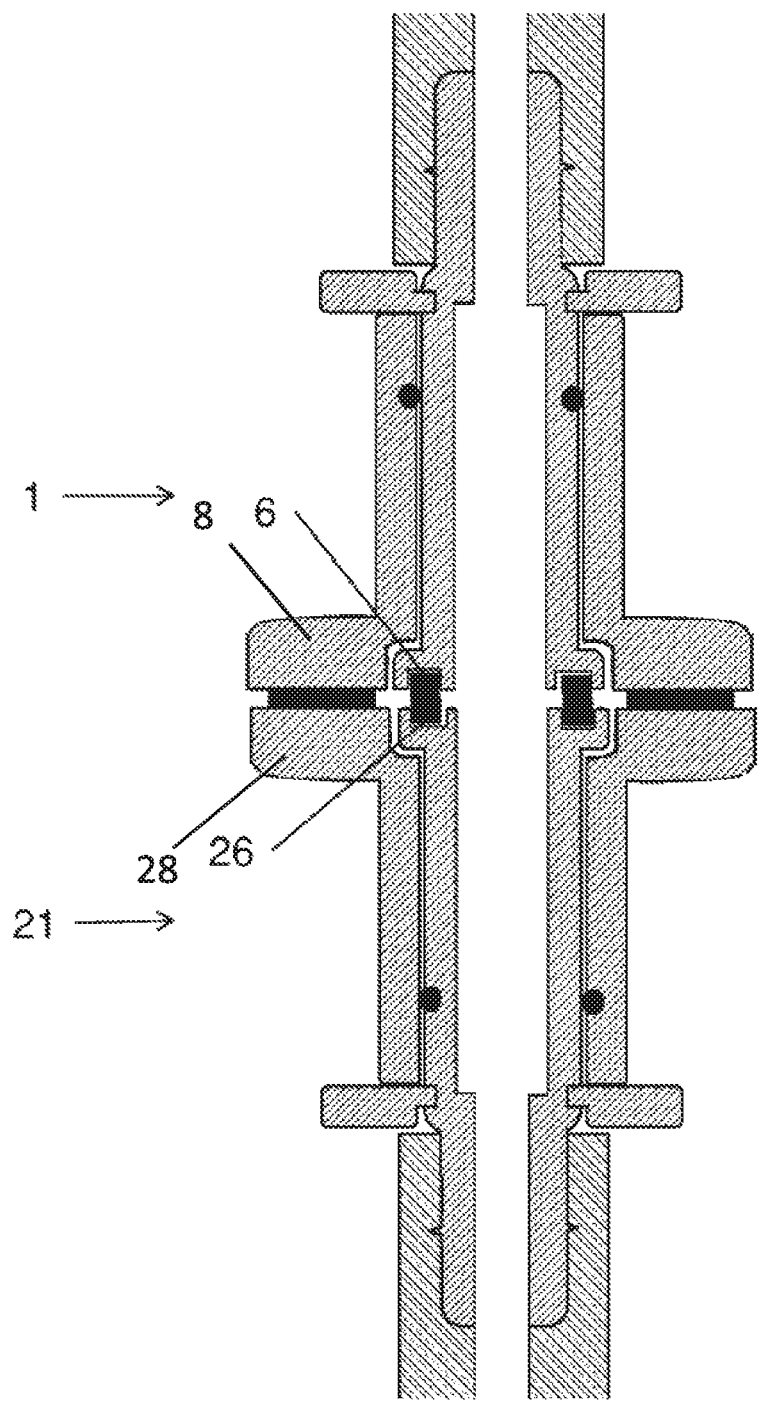
FIG. 2 shows a connection of the invention, obtained by the coupling of two connectors of the invention to each other.

The connector 1 includes a central tubular and elongated stem member 2, which has a line connection end 3 (to which a length of tubing 15 can be firmly attached) and a coupling end 5 where an annular gasket 6, e.g. an O-ring or a gasket with rectangular cross-section, is fitted on the coupling end 5. The annular gasket 6 is arranged to engage a similar annular gasket 26 on a similar second connector 21 (as depicted in FIG. 2) in sealing abutment. Suitably, the annular gasket 6 can extend in a plane transverse to the longitudinal axis of the stem member 2 and it may e.g. be mounted in an annular recess at the extremity of the coupling end 5. From the functional point of view, the stem member 2 provides fluid transport through the tubular center, connection to tubing etc. at the line connection end 3 and sealing towards an opposite connector at the coupling end 5. and;

The connector 1 further includes a tubular socket member 7, which is concentrically arranged outside the stem member 2. The socket member 7 has a flange 8 concentrically arranged outside the coupling end 5 of the stem member 2, wherein the flange 8 comprises a cover film 9 releasably bonded to the flange 8 and covering i) the coupling end 5 of the stem member 2, ii) the annular gasket 6 and iii) at least a portion of the flange 8. The flange 8 suitably extends in a plane transverse to the longitudinal axis of the stem member 2, adjacent to the plane of the annular gasket 6. By covering both the stem member 2 (including its tubular interior), the annular gasket 6 and a substantial part of the flange 8, the cover film 9 seals off the interior of the connector 1 from the ambient surroundings. For this purpose, the cover film 9 suitably is a flexible film which is impermeable to microorganisms. It can be a plastic film or laminate, but it can also be a steam-permeable membrane with a pore size sufficiently small to prevent microorganisms from entering the interior.

Figure 3:
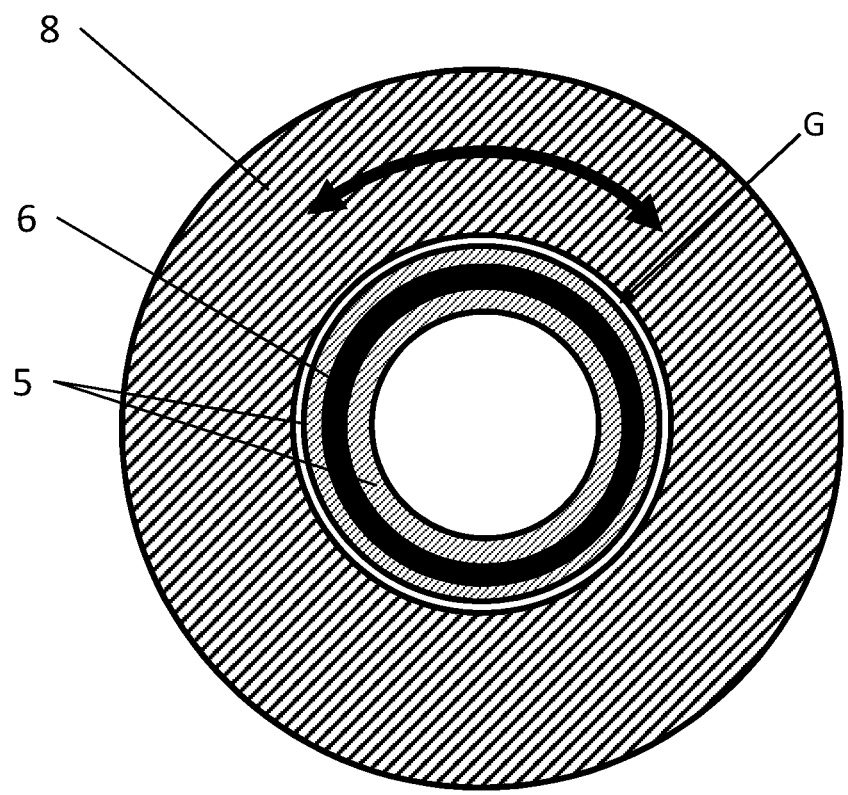
FIG. 3 shows a perspective view of the connector of FIG. 1, that can be implemented within embodiments of the present invention.

As shown in FIGS. 1 and 3, the socket member 7 is freely rotatable around the stem member 2 via an air gap "G" between an inside 11 of the socket member 7 and an outside 12 of the stem member 2. The connector 1 further comprises an annular seal member 10, which can e.g. be an O-ring, in sealing abutment between the inside 11 of the socket member 7 and the outside 12 of said stem member 2. The seal member 10 can be accommodated in a recess on the inside 11 of the socket member 7 or it can alternatively be accommodated in a recess on the outside 12 of the stem member 2. This means that the socket member 7 can be freely rotated around the stem member 2 via the air gap "G" in order to achieve coupling with an opposite coupling without any torsional tension being applied to the firmly connected tubing 15 at the line connection end 3. Aseptic conditions inside the connector 1 are ensured by the annular seal member 10 and the cover film 9. A particular advantage of the arrangement with the annular gasket 6 providing the sealing against the opposite connector 21 (as depicted in FIG. 2) is that the annular seal member 10 is not in contact with any fluid transported through the coupled connector 1, 21 during use. Thus, any contamination potentially present under the seal member 10 after rotation will never reach the fluid.

In some embodiments, the cover film 9 is releasably bonded to said flange 8 via an annular layer 13 of a resilient material, such as a resilient foam. The resilient material can be adhesively bonded to the flange 8 surface with a permanent adhesive and it can on the outside surface have a pressure-sensitive adhesive capable of releasably binding the cover film 9. The adhesives are suitably chosen such that the resilient material stays on the flange 8 when the cover film 9 is removed. The thickness of the resilient material and the position of the annular gasket 6 can be chosen such that a thin gap is formed between the cover film 9 and the gasket 6, but it is also possible to have the gasket 6 in contact with the cover film 9, such that the gasket 6 slides against the cover film 9 upon rotation of the socket member 7. The cover film 9 can be folded over 180 degrees and arranged to be removed by pulling a tab 14. Typically, when two connectors 1, 21 are connected, the cover films 9 of both connectors 1, 21 can be removed pairwise after the connectors 1, 21 have been brought into contact with each other. This requires that the films 9 are folded over and provides a decreased risk of contamination of the interior. To protect the cover film 9, further protective films and/or caps may be applied to the connector 1, 21 and removed before connection.

In some embodiments, the stem member 2 further comprises a recess 17 adapted to receive a locking ring 16, engaging the socket member 7. The locking ring 16 can push the socket member 7 toward the coupling end 5 of the stem member 2 and thus by friction prevent further rotation of the socket member 7 after connection.

In certain embodiments, the flange 8 comprises one or more fastening means arranged to engage or mate with one or more fastening means on the flange 28 of a similar second connector 21 (as depicted in FIG. 2). The fastening means can hold the two connectors 1, 21 together, either permanently or temporarily until a clamp has been applied over the flanges (see below). The fastening means can e.g. be male-female snap-in devices, but can also be selected among a large number of other fastening devices known in the art. One connector can e.g. have one or more latch members arranged to engage one or more latch frames on the other connector. If male-female fastening means are used, each connector may suitably have both a male and a female fastening member in different positions, arranged to mate with their counterparts on the other connector. This allows for fastening of identical connectors against each other.

In some embodiments, the flange 8 is arranged to be clamped together with the flange 28 of a similar second connector 21. The clamp can typically be a fold-over clamp covering the circumferences of both flanges. Suitable clamps are well known under various names, such as BioClamp™, ReadyClamp™, Tri-clamp, Tri-clover etc.

In certain embodiments, the line connection end 3 of the stem member 2 comprises tubing fixation means, such as a hose barb 4. This allows firm connection of tubing to the line connection end 3. Alternatively, the tubing fixation means can be another coupling such as e.g. a conventional Tri-clamp or Tri-clover coupling for attachment of tubing or any other device to the connector 1.

The connector 1 of the invention is suitably connected to a device, a length of tubing or a tubing system through the line connection end 3 and the assembly can then be packaged in a sealed package and pre-sterilized, e.g. by gamma irradiation or autoclaving. The materials of construction are suitably chosen such that they withstand the particular sterilization conditions used without formation of undesirable leachables. The materials can typically be plastics, elastomers and adhesives conforming to the USP VI criteria of the US Pharmacopeia. As the adhesives do not come into contact with any fluids conveyed through the connection, the requirements on them may be less severe than for the fluid-contact materials. Examples of plastics to be used can be polycarbonate and polysulfone, while an example of an elastomer is silicone rubber.

In use, two pre-sterilized connectors 1, 21 with attached tubing etc. are approached to each other and at least one of the socket members 7 is rotated so that the cover films 9 of both connectors 1, 21 are aligned with each other and any fastening members can be engaged to each other. The two cover films 9 are then removed either before or after engagement of the fastening members. If a clamp is used it is applied to the connection and if a locking ring 16 is used it is applied to lock the rotational movement.

As further shown in FIG. 2, in one aspect the present invention discloses a connection comprising two connectors 1,21 as disclosed above, connected such that the annular gaskets 6,26 are engaged in sealing abutment with each other. The connection may further comprise a clamp (not shown) arranged around the flanges 8,28.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A connector for substantially aseptic connection of tubing, said connector comprising:
   a central tubular stem member comprising a tubular center, a line connection end for firmly attaching a length of tubing thereto and a coupling end with an annular gasket arranged to engage a similar annular gasket on a second connector in sealing abutment and configured to provide fluid transport through the tubular center, connection to the tubing and sealing towards the second connector;
   a tubular socket member, concentrically arranged along a parallel axis around an outside of said stem member creating an air gap between an inside of said socket member and an outside of said stem member, and having a flange concentrically arranged outside said coupling end and comprising a cover film releasably bonded to said flange and covering said coupling end of said stem member, said annular gasket and at least a portion of said flange; wherein during facilitation of connection, said connector is approached with said second connector and said socket member of said connector is configured to rotate around said stem member via the air gap so that the cover film is aligned with a corresponding cover film of the second connector and to perform coupling with said second connector;
   an annular seal member in sealing abutment between the inside of said socket member and the outside of said stem member; and
   a locking ring configured to hold said socket member in place to prevent further rotation after connection of said connector with said second connector, wherein said stem member further comprises a recess along an exterior surface thereof adjacent to the line connection end to receive the locking ring to thereby engage the socket member by pushing said socket member towards the coupling end of the stem member to prevent further rotation of said socket member, after connection.

2. The connector of claim 1, wherein said cover film is releasably bonded to said flange via an annular layer of a resilient material.

3. The connection of claim 2, wherein the resilient material comprises a resilient foam.

4. The connector of claim 1, wherein said cover film is folded over and arranged to be removed by pulling a tab.

5. The connector of claim 1, wherein the stem member further comprises a recess adapted to receive a locking ring, engaging said socket member.

6. The connector of claim 1, wherein said annular seal member is accommodated in a recess on the inside of said socket member.

7. The connector of claim 1, wherein said annular seal member is accommodated in a recess on the outside of said stem member.

8. The connector of claim 1, wherein the line connection end comprises tubing fixation means.

9. The connection of claim 8, wherein the tubing fixation means a hose barb.

10. A connection comprising two connectors according to claim 1, connected such that the annular gaskets are engaged in sealing abutment with each other.

* * * * *